0

(12) United States Patent
Aksenova et al.

(10) Patent No.: US 8,620,420 B2
(45) Date of Patent: Dec. 31, 2013

(54) METHOD FOR FILTERING OUT ARTEFACTS OF DEEP BRAIN STIMULATION

(75) Inventors: Tetiana Aksenova, Grenoble Cedex (FR); Dimitri Nowicki, Amherst, MA (US); Alim-Louis Benabid, Grenoble Cedex (FR)

(73) Assignee: Institute National de la Sante et de la Rescherche Medicale (INSERM), Paris (FR)

( * ) Notice: Subject to any disclaimer, the term of this patent is extended or adjusted under 35 U.S.C. 154(b) by 942 days.

(21) Appl. No.: 12/597,196

(22) PCT Filed: Apr. 24, 2008

(86) PCT No.: PCT/EP2008/055012
§ 371 (c)(1),
(2), (4) Date: Mar. 25, 2010

(87) PCT Pub. No.: WO2008/132136
PCT Pub. Date: Nov. 6, 2008

(65) Prior Publication Data
US 2010/0185257 A1    Jul. 22, 2010

(30) Foreign Application Priority Data
Apr. 26, 2007   (EP) .................................... 07300991

(51) Int. Cl.
*A61B 5/04*    (2006.01)
(52) U.S. Cl.
USPC ........................................................ 600/544
(58) Field of Classification Search
USPC .................................................. 600/544–545
See application file for complete search history.

(56) References Cited

U.S. PATENT DOCUMENTS

| 6,529,774 | B1 | 3/2003 | Green |
| 2005/0119703 | A1 | 6/2005 | DiLorenzo |

(Continued)

FOREIGN PATENT DOCUMENTS

WO    2006017053 A1    2/2006

OTHER PUBLICATIONS

D. V. Nowicki, A.-L. Benabid, and T. I. Aksenova. Adaptive Model for Filtering of Stimulation Artifacts in Multichannel Records of Neuronal Activity. Sep. 16, 2007. International Conference of Numerical Analysis and Applied Mathematics. AIP Conf. Proc. 936, pp. 382-386.*

(Continued)

*Primary Examiner* — Navin Natnithithadha
*Assistant Examiner* — Etsub Berhanu
(74) *Attorney, Agent, or Firm* — Pepper Hamilton LLP

(57) ABSTRACT

The present invention relates to a method for filtering the signal of neuronal activity during a high frequency deep brain stimulation (DBS) to remove the stimulus artefact in the observed signal, comprising the step of approximating the observed signal trajectories in phase space the observed signal being considered as a sum of the stimulation artifacts induced by the signal of stimulation, wherein the signal of stimulation is assumed to be a solution of an ordinary differential equation including a self-oscillating system with stable limit cycle; slicing the observed signal and its derivative into segments, each segment corresponding to a period of stimulation; collecting N selected periods of stimulation to a training set; estimating the limit cycle of the self-oscillating system; synchronizing each artefact of the observed signal with the estimated limit cycle; subtracting the estimated limit cycle from each artefact in phase space according to the synchronization; collecting all segments in order to obtain whole filtered signal and finally presenting the results in time domain.

18 Claims, 11 Drawing Sheets

(56) References Cited

U.S. PATENT DOCUMENTS

Figure 1:
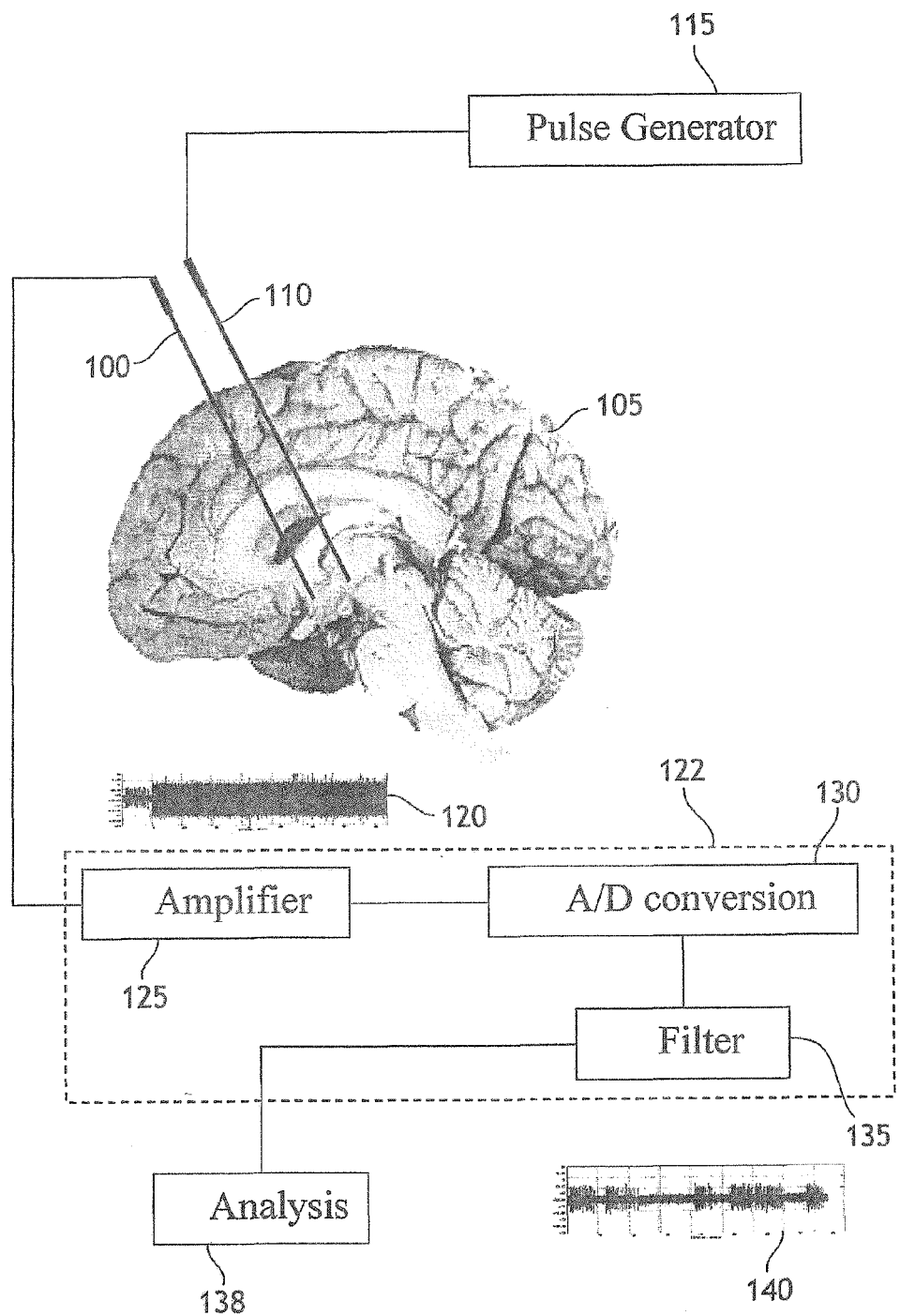

| | | |
|---|---|---|
| 2006/0114841 A1 | 6/2006 | Date et al. |
| 2006/0149337 A1 | 7/2006 | John |
| 2006/0167369 A1 | 7/2006 | Montgomery et al. |

OTHER PUBLICATIONS

Hashimoto, T., et al., Stimulation of the subthalamic nucleus changes the firing pattern of pallidal neurons, Journal of Neuroscience, Mar. 1, 2003;23(5):1916-23.

International Search Report of PCT/EP2008/055012 dated Jul. 8, 2008.

Hashimato Takao et al, "A template subtraction method for stimulus artefact removal in high-frequency deep brain stimulation," Journal of Neuroscience, 113, 2001, 181-186.

Gudzenko Li, "Statistical method for self-oscillating system characteristics detection," Izvestiia Vuzov Radiophysics, vol. 5, 573-587, 1962.

T. Aksenova et al, "Filtering out of Artifacts of Deep Brain Stimulation Using Nonlinear Oscillattory Model", Neural Computation 21, 2648-2666.

Benabid A.L. et al "A putative generalized medel of the effects and mechanism of action of High Frequency Electrical Stimulation of the Central Nervuos System," Acta. neurol. Belg., 2005, 105 : 149-157.

McIntye C.C. et al "Cellular effects of deep brain stimulation : model-based analysis of activation and inhibition," J. Neurophysiol., 2003, 91: 1457-1469.

Aksenova, T.I. et al "An unsupervised automatic method for sorting neuronal spike waveforms in awake and freely moving animals," Method, 2003, 30: 178-187.

* cited by examiner

| Record # | NSR | ASR | ASR after filtering in time domain | ASR after filtering in phase space |
|---|---|---|---|---|
| 2548 | 0.34 | 2.2 | 0.8 | 0.4 |
| S1529 | 0.27 | 6.1 | 1.6 | 0.62 |
| F096K | 0.15 | 9.1 | 1.8 | 0.9 |
| N0047 | 0.22 | 5.05 | 0.95 | 0.56 |
| N0023 | 0.20 | 5.22 | 1.01 | 0.61 |

FIG.14

| Record # | Filtering in time domain | | Filtering in phase space | |
|---|---|---|---|---|
| | Max. STD | Sum of STDa across residual | Max. STD | Sum of STDa across residual |
| 2548 | 0.334 | 8.34 | 0.105 | 3.76 |
| S1529 | 0.508 | 6.57 | 0.118 | 2.51 |
| F096K | 0.880 | 10.22 | 0.165 | 4.04 |
| N0047 | 0.088 | 3.52 | 0.076 | 1.84 |
| N0023 | 0.145 | 3.96 | 0.102 | 2.40 |

FIG.15

STD of artefact residuals in the artefact peak zone

| # | Filtering in time domain | | Filtering in phase space | |
|---|---|---|---|---|
| | Max. STD | Sum of STDa across residual | Max. STD | Sum of STDa across residual |
| 2548 | 0.106611 | 4.34 | 0.057173 | 1.76 |
| S1529 | 0.118543 | 2.57 | 0.058254 | 1.251 |
| F096K | 0.088063 | 6.22 | 0.018505 | 2.04 |
| N0047 | 0.151444 | 3.52 | 0.095315 | 1.84 |
| N0023 | 0.14377 | 3.96 | 0.072804 | 2.20 |
| DUG1581 | 0.086437 | 3.86 | 0.051635 | 1.935 |
| DUG4821 | 0.201742 | 3.88 | 0.147963 | 2.18 |
| S467 | 0.037689 | 1.646 | 0.023234 | 0.822 |

…

METHOD FOR FILTERING OUT ARTEFACTS OF DEEP BRAIN STIMULATION

CROSS-REFERENCE TO RELATED APPLICATIONS

This application is the U.S. National Stage filing of International Application Serial No. PCT/EP2008/055012 filed Apr. 24, 2008, which claims priority to European Application No. 07300991.2 filed Apr. 26, 2007, each of which is incorporated herein by reference in its entirety.

The present invention pertains to processing of brain signals, and, more particularly, to methods and systems for processing brain signals representing multiple signals.

High-frequency (100-300 Hz) Deep Brain Stimulation (DBS) is a surgical procedure for treating a variety of disabling neurological symptoms, such as the debilitating symptoms of Parkinson's disease, for instance.

During a DBS, electrical impulses of stimulation are delivered to a target zone in the brain of a patient.

A resulting problem of DBS is that the neuronal activity (reported by neuronal action potentials AKA spikes) of the patient can not be measured during the stimulation period. Large stimulus artefacts hamper spike detection leading to problems in analyzing single cell activity during stimulation.

The specific signal of neuronal activity and the artefact of stimulation stack on one another in the record.

The artefacts of stimulation have common waveform but are not identical due to sampling errors and irregularities of stimulus production. The Artefact to Signal Ratio (ASR)—which is the ratio of mean of amplitudes of artefacts of stimulation to the averaged amplitude of spikes of neuronal activity observed before stimulation—is comprised in the range of 5-20.

In order to avoid this problem, which is recurrent in the field of electrophysiology, several methods have been developed in order to achieve this artefact suppression. Among them, a recent method has been described by Hashimoto et al (Hashimoto T, Elder C. M., Okun M. S., Patrick S. K., Vitek J. L., Stimulation of the subthalamic nucleus changes the firing pattern of pallidal neurons, *J. Neurosci.*, 2003, 23:1916-1923) for subtracting artefacts of stimulation in a record.

This method is based on making an artefact template via averaging a set of peri-stimulus segments, according to the following general protocol.

In order to take into account artefact variability several templates were created. The signal presented as an example had the ASR approximately equal to six, that means that artefact amplitude is six times greater than spikes.

After template subtraction, the signal still contains artefact residuals 1.5-2 times greater than spikes. Size of the residuals in the time domain was about 0.8 s. These windows were removed from the signal before further analysis. Therefore, this part (about 11% of record time) is not longer available for spike sorting or any further analysis. Such a cut-off can significantly corrupt spike trains obtained from analyzed record.

The accompanying drawings, which are incorporated in and constitute a part of this specification, illustrate various embodiments of the present invention, and, together with the description, serve to explain the principles of the invention.

Figure 2:
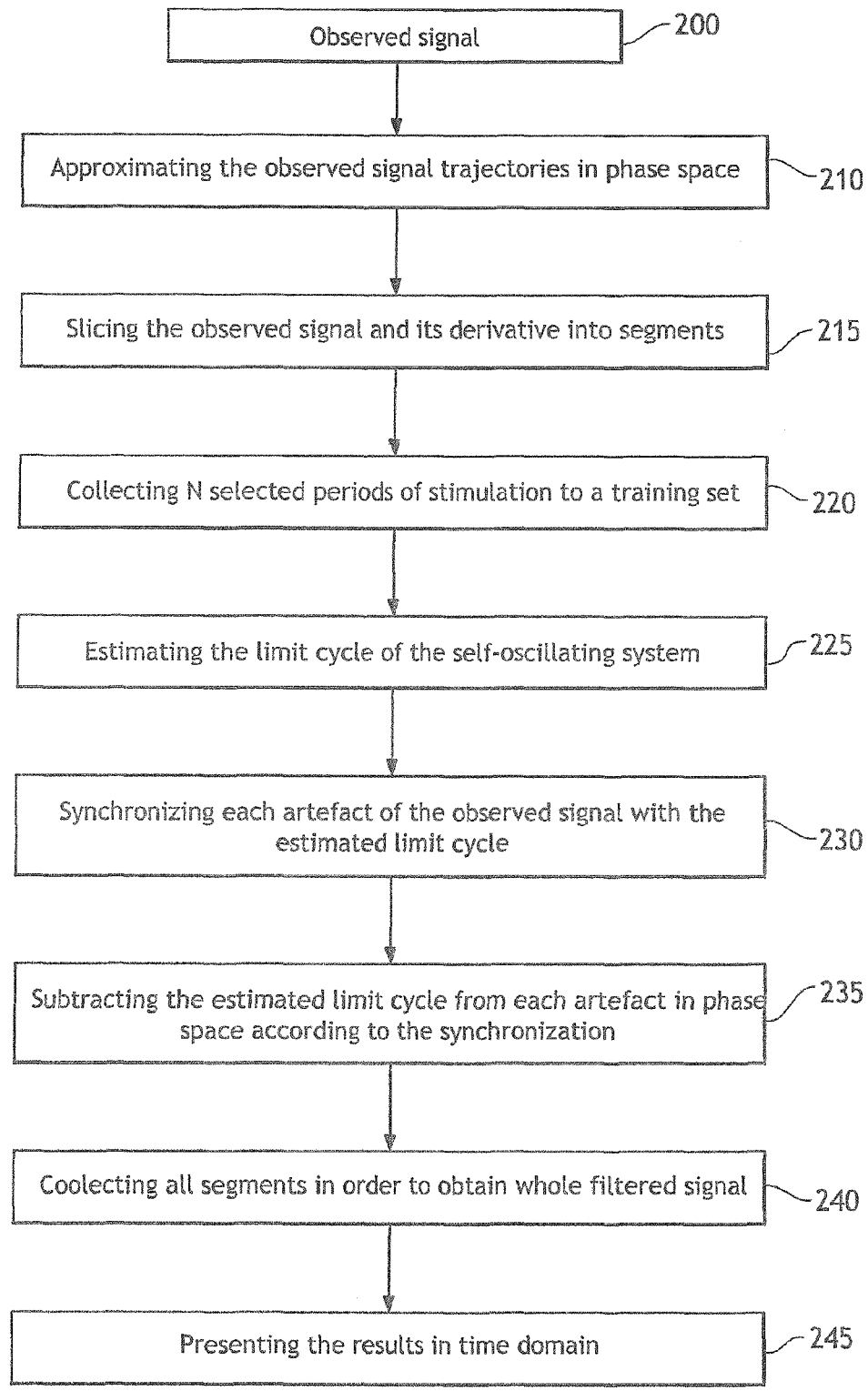
Figure 3:
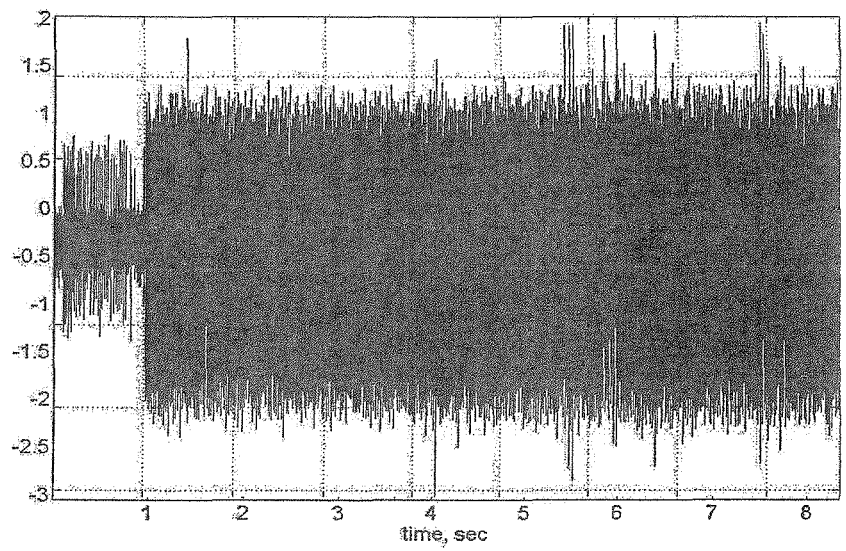
Figure 4:
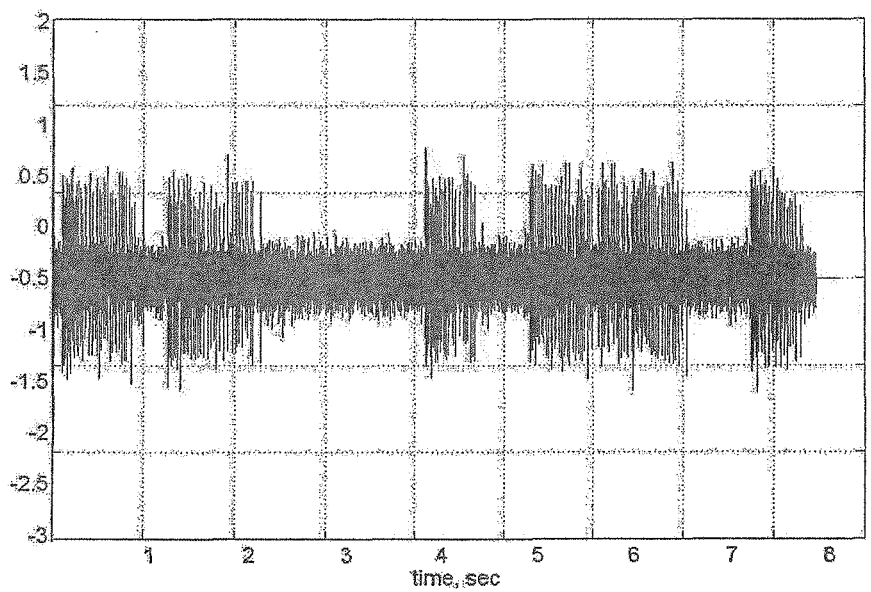
Figure 5:
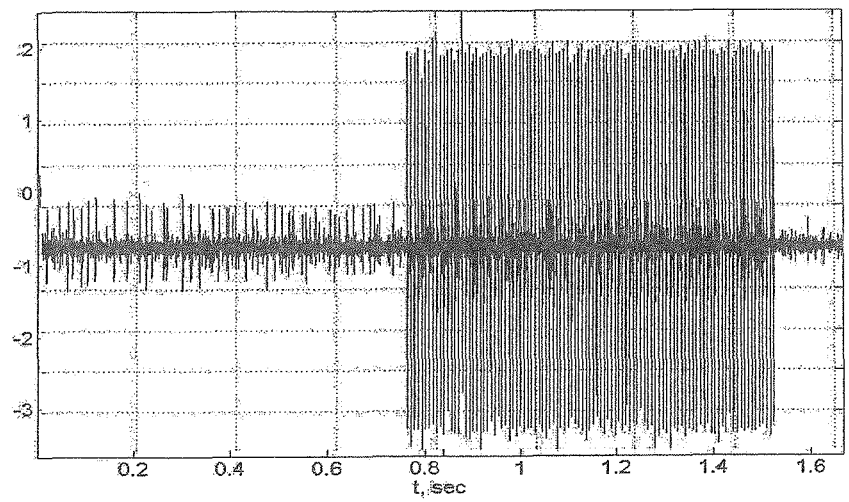
Figure 6:
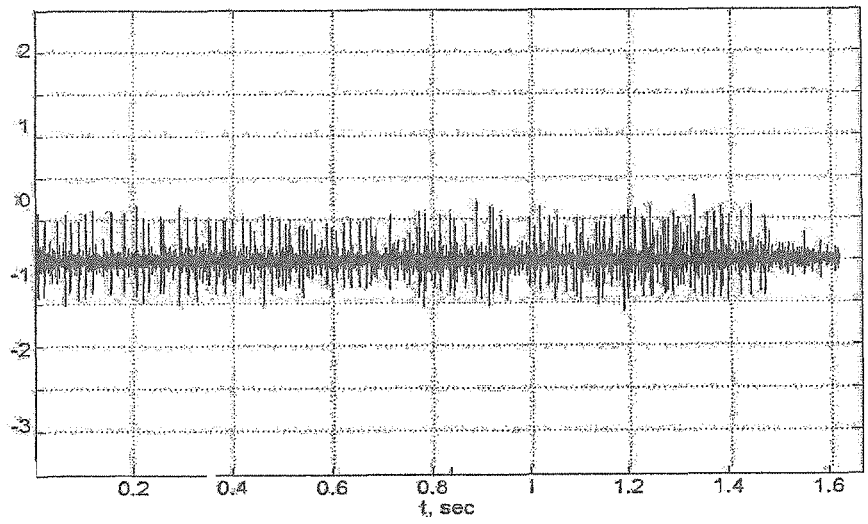
Figure 7:
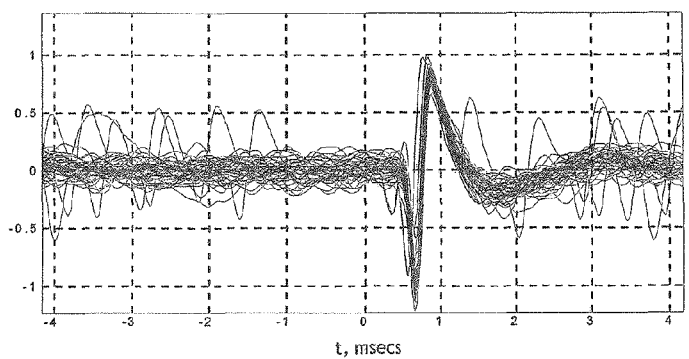
Figure 8:
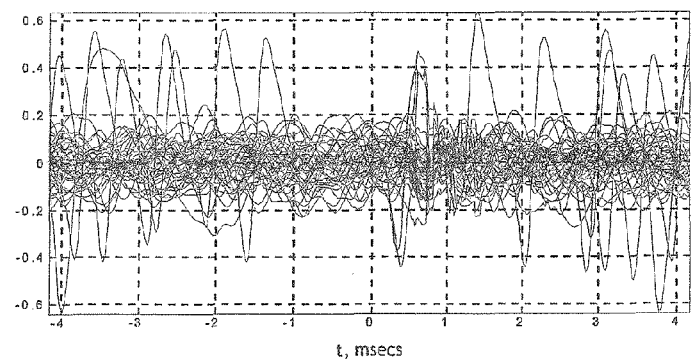
Figure 9:
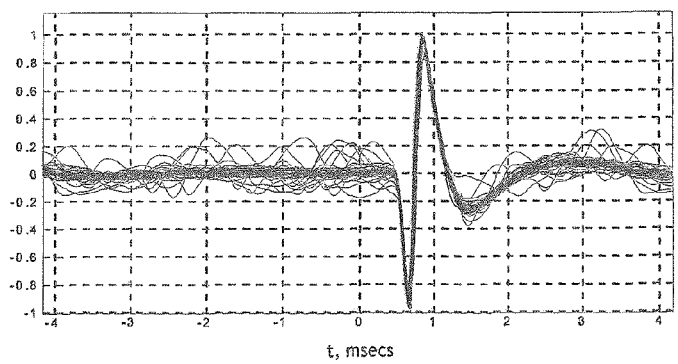
Figure 10:
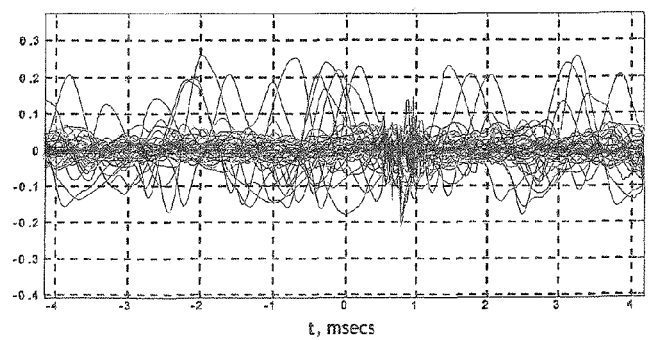
Figure 11:
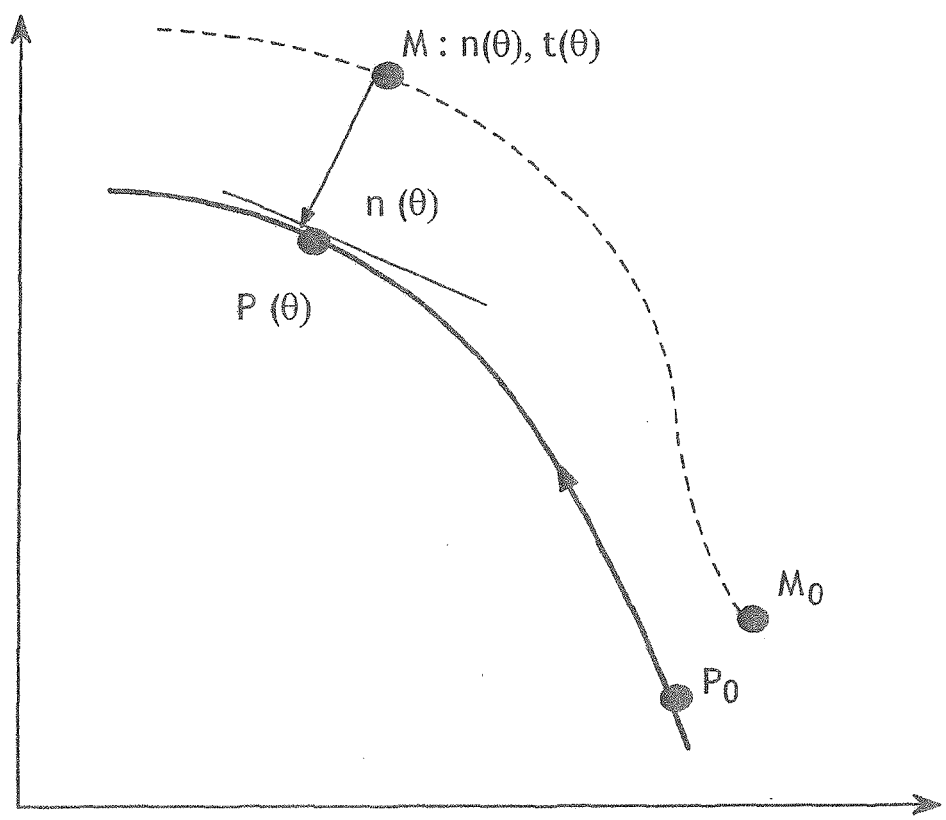
Figure 12:
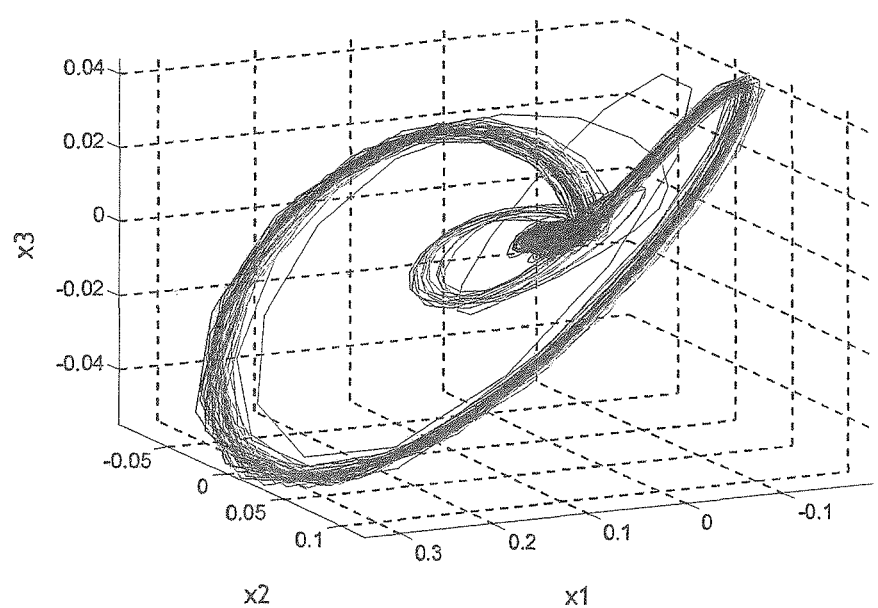
Figure 13:
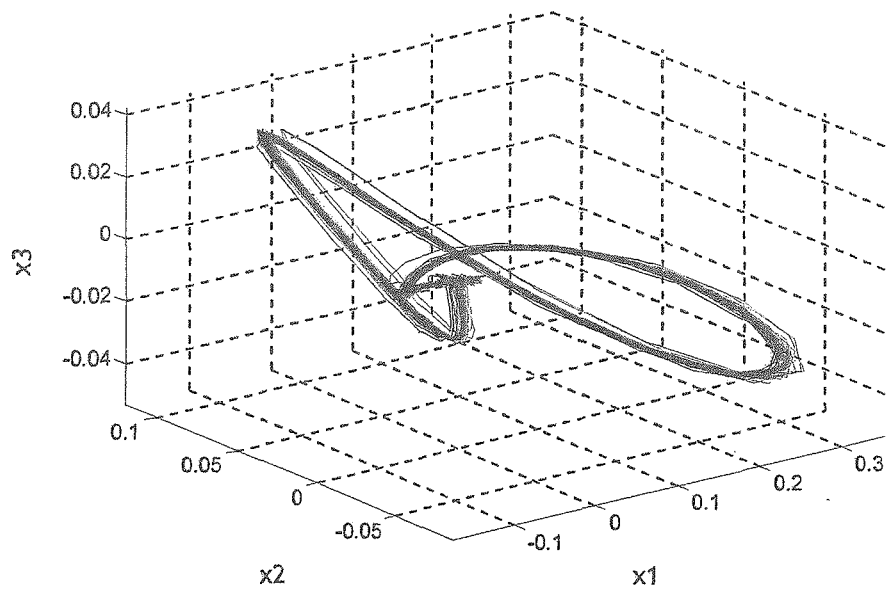
Figures 16, 17:
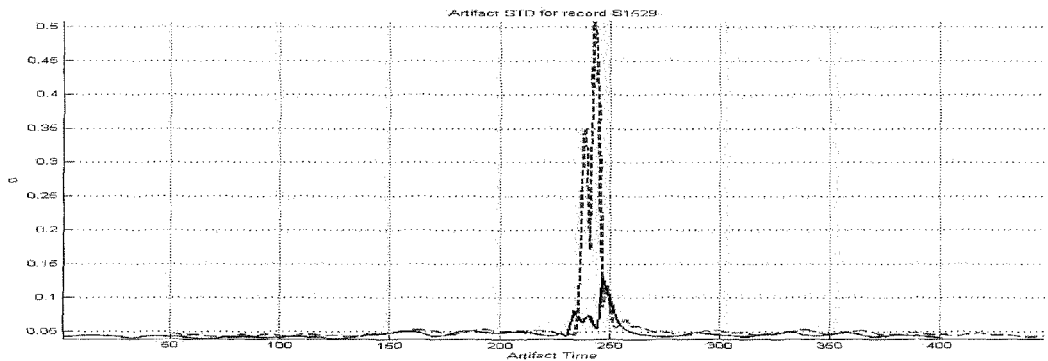
Figure 18:
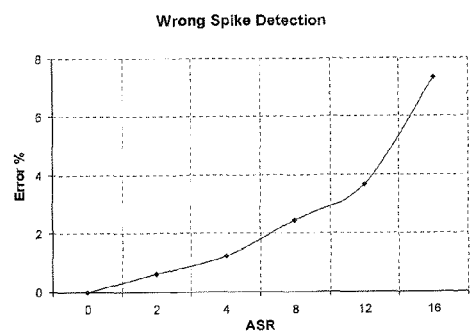
Figure 19:
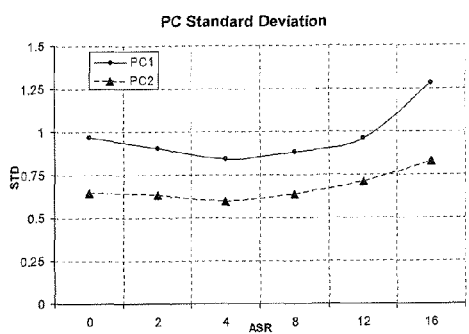
Figure 20:
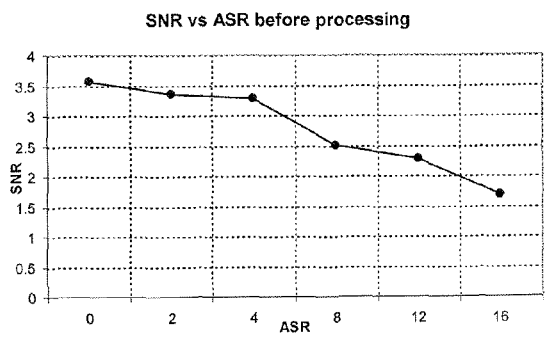
Figure 21:
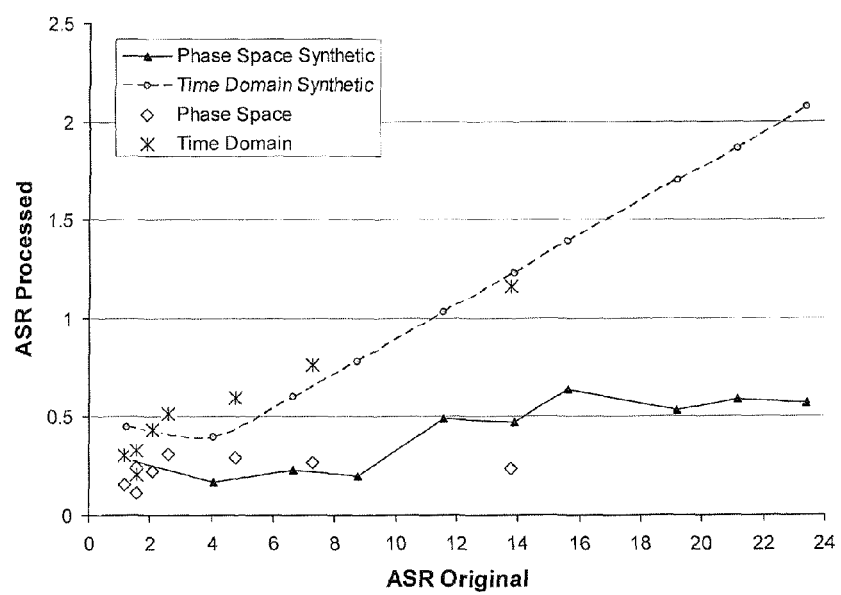

FIG. 1 is a schematic representation of the system for filtering the signal of neuronal activity during a high frequency deep brain stimulation (DBS) to remove the stimulus artefact in the observed signal according to the invention, FIG. 2 is a block diagram of the method for filtering the signal of neuronal activity during a high frequency deep brain stimulation (DBS) according to the invention, FIG. 3 is a representation of a first signal of neuronal activity before and during DBS, FIG. 4 is a representation of the first signal of neuronal activity before and during DBS of FIG. 3 after filtering, FIG. 5 is a representation of a second signal of neuronal activity before and during DBS, FIG. 6 is a representation of the second signal of neuronal activity before and during DBS of FIG. 5 after filtering, FIG. 7 is a representation of a first signal sliced into the stimulation-period windows before filtering, FIG. 8 is a representation of the first signal of FIG. 7 sliced into the stimulation-period windows after filtering, FIG. 9 is a representation of a second signal sliced into the stimulation-period windows before filtering, FIG. 10 is a representation of the second signal of FIG. 7 sliced into the stimulation-period windows after filtering, FIG. 11 is a representation of the local coordinates in the neighbourhood of stable limit cycle, FIG. 12 is a representation of artefact trajectories in the phase space projection with coordinates equal to first, second, and third derivative for a first record, FIG. 13 is a representation of artefact trajectories in the phase space projection with coordinates equal to first, second, and third derivative for a second record, FIG. 14 is a table showing the Artefact Spike Ratio (ASR) before and after signals filtering, FIG. 15 is a table showing the standard deviations (STD) of artefact residuals in the peak zone FIG. 16 is a representation of the phase-dependent artefact STDs based on the representation of signal by the model with additive noise (dash line) and by the nonlinear model of oscillations (continuous line), FIG. 17 is a table showing STD of artefact residuals in the artefact peak zone, FIG. 18 is a representation of the percentage of errors of spike detection after filtering, FIG. 19 is representation of the variance of the first two principal components for detected spikes, FIG. 20 is a representation of SNR (Spike-Noise Ratio) in synthetic signals used for the test, FIG. 21 is a representation of the Residual-spike ratio depending on pre-filtering ASR comparing time-domain and phase-space algorithms for synthetic and real data wherein the results for eight real records (markers) and synthetic signals (dash and continuous lines) are in a good fit.

Reference will now be made in detail to exemplary embodiments of the invention, which are illustrated in the accompanying drawings. Wherever possible, the same reference numbers will be used throughout the drawings to refer to the same or like parts.

Referring to FIG. 1, showing an example of an experimental situation where recording and stimulation are simultaneously performed, the device comprises a glass-coated platinum-iridium microelectrode or similar 100 and inserted in a structure of the cerebral hemisphere of a brain 105 for single (or multiple) unit recording. For example, the microelectrode is inserted in the internal palladium or any other nucleus or cortex or white matter. Through the mircroelectrode 100, a stimulating electrode 110 (which could be another microelectrode or a chronic macroelectrode) is implanted within a cerebral structure (such as the subthalamic nucleus, for instance). The contacts of the electrode 110 are connected to a programmable pulse generator 115, generally called a stimulator.

The signal 120 has been recorded by the electrode 100 using an electrophysiological acquisition system 122 including an amplifier 125, an A/D conversion unit 130, associated to a filter 135 for example. This produces the said filtered signal 120

Moreover, the device includes an analysis unit 138 to analyse said filtered signal 120. The analysis unit 138 which is a computer program, i.e. an algorithm (usually installed and executed in a computer or included as a module in the acquisition system 122) produces the signal 140 where the artefact of stimulation has been removed from signal 120.

Referring now to FIG. 2, the method for filtering the signal of neuronal activity during high frequency deep brain stimulation (HF-DBS) to remove the stimulus artefact from the observed signal, comprises the step 200 of recording the observed signal 120.

At step 210, the first, second and third derivatives of the observed signal are calculated, using one of the methods, including convolutions, in particular Gaussian convolution to approximate the observed signal trajectories in phase space. The derivatives serve to present signal trajectory in the phase space. The Gaussian convolution is calculated for a characteristic frequency comprised between 3 and 4 kHz, and preferentially for a characteristic frequency equal to 3.52 kHz. The observed signal is supposed to be the sum of the electrophysiological signal, the stimulation signal (artefacts induced by the signal of stimulation) and background noise.

The signal of stimulation is assumed to be a solution of an ordinary differential equation describing a self-oscillating system with stable limit cycle.

At step 215 the observed signal and its derivatives are sliced into segments, each segment corresponding to a period of stimulation. Furthermore, the center of each time segment is near to the highest of signal peaks in the observed signal.

Moreover, at step 220, N selected periods of stimulation are collected to a training set, said training set comprising at least 1000 artefacts of simulation and at step 225 the limit cycle of the self-oscillating system is estimated. The limit cycle of the self-oscillating system is estimated by using the element from training set that provides the maximum of probability density in the neighbourhood. Any other consistent statistics using the elements of the training set can be applied also. Preferentially, the self-oscillating system with stable limit cycle is a self-oscillating system of forth order.

Then, at step 230, each artefact of the observed signal is synchronized with the estimated limit cycle, and at a step 235, the estimated limit cycle is subtracted from each artefact in phase space according to the synchronization.

Finally, at a step 240, all segments are collected in order to obtain whole filtered signal, and at a step 245 the results are presented in time domain (signal 140).

Method's Principle:

We consider observed signal $x(t)$, $t=1, 2, \ldots$ as a sum of the stimulation artefacts $x_{St}(t)$ and the signal $x_{Nr}(t)$ of neuronal activity: $x(t)=x_{St}(t)+x_{Nr}(t)$. The signal of stimulation assumed to be a solution of an ordinary differential equation with perturbation $$\frac{d^n x_{St}}{dt^n} = f\left(x, \ldots, \frac{d^{n-1} x_{St}}{dt^{n-1}}\right) + F\left(x_{St}, \ldots, \frac{d^{n-1} x_{St}}{dt^{n-1}}, t\right), \quad (2)$$

where n is the order of the equation, F( ) is a perturbation function and equation $$\frac{d^n x_{St}}{dt^n} = f\left(x_{St}, \ldots, \frac{d^{n-1} x_{St}}{dt^{n-1}}\right) \quad (3)$$

describes a self-oscillating system with stable limit cycle $x^0(t)=(x_1^0(t), \ldots, x_n^0(t))+$, $0<t\leq T$, in phase space with coordinates $$x_1 = x_{St}, x_2 = \frac{dx_{St}}{dt}, \ldots, x_n = \frac{d^{n-1} x_{St}}{dt^{n-1}}.$$

Here T is the period of stable oscillations that is the period of stimulation. The perturbation function F( ), bounded by a small value, is a random process with zero mean and small in the comparison to the period of stable oscillations correlation time: $B(F(\cdot, t), F(\cdot, t+\Delta t))\approx 0$ if $\Delta t > \Delta t_{corr}$, $\Delta t_{corr} \ll T$.

In the case of stable oscillations (Eq. 3) the trajectory of the signal tends to the limit cycle whenever it is found in the neighbourhood. It provides the periodic solution if the initial point locates on the limit cycle. The perturbation function F( ) in Eq. (2) tends to displace the trajectories of the signal out from the limit trajectory. However, if the perturbation is small enough the trajectories stay in the neighbourhood of the limit cycle $x^0(t)$, $0<t\leq T$ i.e., the solutions of Eq. (2) are similar to one another but they never coincide.

Let us introduce the local coordinates in the neighbourhood of the limit cycle following (Gudzenko, L. I., Statistical method for self-oscillating system characteristics detection, *Izvestiia Vuzov Radiophysics*, vol. 5, pp. 573-587, 1962). Let us fix an arbitrary point on the limit cycle $P_0$ as a starting point.

Referring to FIG. 11, The position of any arbitrary point P on the limit trajectory can be described by its phase $\theta$, which is a time movement along the limit cycle from a starting point $P_0$, defined as $P_0(\theta=0)$. Let us assume that function f( ) in Eq. (2, 3) is twice continuously differentiable on all the arguments of the function, thus providing a necessary smoothness. At a point P with phase $\theta$ it is possible to construct a hyperplane (and only one such hyperplane) that is normal to the limit cycle. Let us consider an arbitrary trajectory Eq. (2) in the neighbourhood of limit cycle.

Denote $M(\theta)$ the point of its intersection to the hyperplane of phase $\theta$ and set the point of phase zero $M(0)$, $\theta=0$ as the initial point for analyzed trajectory. Any trajectory can be described by variables $n(\theta)$ and $t(\theta)$ (FIG. 11) where $n(\theta)$ is a vector of normal deviation defined by $M(\theta)$ and its orthogonal projection $P(\theta)$ on the limit cycle. The second variable $t(\theta)$ is a time movement along the trajectory from the initial point $M(0)$ to the analyzed point $M(\theta)$. Thus, the limit trajectory is defined by $n(\theta)=0$ and $t(\theta)=\theta$, where 0 is a vector with all components equal to 0.

Let $\gamma(\theta)$ be the phase deviation, $\gamma(\theta)=t(\theta)-\theta$. Eq. (2) could be rewritten in linear approximation (Gudzenko 1962) in the deviations $n(\theta)$ and $\gamma(\theta)$ as follows:

$$n(\theta)/d\theta + N[n] = F_n(\theta)$$

$$d\gamma/d\theta + (\Theta \cdot n) = F_\gamma(\theta). \quad (4)$$

Here $N(\theta)$ and $\Theta(\theta)$ are the functions of the parameters. As a result signal trajectory in phase space is presented in linear approximation as a sum of periodic component of limit cycle and function of deviation $x(t(\theta))=x^0(\theta)+n(\theta)$, where $n(\theta)$ and $t(\theta)=\gamma(\theta)-\theta$ are followed to Eq. 4. Note that according to the method of the invention, the model of nonlinear oscillations with perturbations (Eq. 2) explains the distortion of both amplitude and phase (Eq. 4).

For the following artefacts filtering the limit cycle that presents a periodic component of signal should be estimated. Limit cycle is described as $x^0(\theta)$, $0<\theta\leq T$, phase running from 0 to T. Let us consider the segments of an arbitrary signal trajectory $x^i(t(\theta))$, $0<\theta\leq T$ with phase $\theta$ running from 0 to T, referred to as a cycles. General population $X=\{x^i(t(\theta)), 0<\theta\leq T\}$ is formed by cycles and corresponds to the realizations of the artefacts of stimulation. The limit trajectory $x^0(\theta)$, $0<\theta\leq T$ corresponds to an ideal "undisturbed artefact of stimulation". The arbitrary cycle is presented as $$x^i(t(\theta))=x^0(\theta)+n^i(\theta), 0<\theta\leq T \quad (5)$$

were $n^i(\theta)$ is determined by (Eq. 4). The mean trajectory converges to the limit cycle $x^0(\theta)$ in linear approximation if the number of averaged trajectories increases infinitely (Gudzenko, L. I., Statistical method for self-oscillating system characteristics detection, *Izvestiia Vuzov Radiophysics*, vol. 5, pp. 573-587, 1962).

It allows estimating the limit cycle $x^0(\theta)$ by calculating the mean of the observed cycles $x^i(t(\theta))$, $0<\theta\leq T$ in the phase space.

$$\tilde{x}^0(\tilde{\theta}) = \frac{1}{k}\sum_{i=1}^{k} x^i(t_i(\theta)), \tilde{\theta} = \frac{1}{k}\sum_{i=1}^{k} t_i(\theta). \quad (6)$$

Another statistics could be also used taking into account that $n^i(\theta)$ and $\gamma^i(\theta)$ are characterized by an asymptotically Gaussian distribution for any $\theta$ in case of uncorrelated noise F( ) (Gudzenko, L. I., Statistical method for self-oscillating system characteristics detection, *Izvestiia Vuzov Radiophysics*, vol. 5, pp. 573-587, 1962).

After the estimation of the mean of the artefacts of stimulation $\tilde{x}^0(\tilde{\theta})$ in phase space it is subtracted from the signal. To this aide local coordinates $t^i(\tilde{\theta})$ are calculated for each cycle. Then functions of vectors of normal deviations $n^i(\tilde{\theta})=x^i(t^i(\tilde{\theta}))-\tilde{x}^0(\tilde{\theta})$, $0<\tilde{\theta}\leq T$ presents the signal after filtering in phase space. The first coordinate of normal deviations presents the residuals of artefacts in time domain $x_{filt}(t)=n_1(t)+x_{Nr}(t)$, $t=1, 2, \ldots$. Spline interpolation is used for regular partition in time.

Algorithm of the Filter and its Implementation:

The implemented algorithm has following steps:

1. Approximate the signal trajectories in phase space. For this purpose we compute smoothed signal and approximation of signal derivatives using Gaussian convolution. So, the derivatives $x^{(k)}(t)$, $k=0, 1, \ldots, n-1$ are approximated by $$D^k x(t) = \int_{-\infty}^{\infty} x(s)\frac{d^k}{dt^k}(\exp((t-s)^2/2\alpha^2))ds \quad (7)$$

2. Slice the signal and its derivatives into the periods of stimulation. Each of the segments contains the separate artefact. Center of each time segment is near to the highest of signal peaks.
3. Collect N randomly selected periods of stimulation to the training set $X_N$.
4. Estimate limit cycle. In case of symmetrical unimodal distribution density mathematical expectation $x^0$ provides the maximum of probability in their neighbourhood, $$P(d(x,x^0)<R) \to \max. \quad (8)$$

According to (Eq. 8) the element from training set that provides the maximum of probability density in the neighbourhood were used to estimate limit cycle $$\tilde{x}^0 = \underset{x \in X_N}{\mathrm{argmax}}|\{y \in X_N : d(x, y) < R\}|, \quad (9)$$

where $|\cdot|$ is the number of elements of the set.

Cycles $x(\theta)$, $0<\theta\leq T$ belong to $\Re^{nT}$ and Euclidian distance in $\Re^{nT}$ was employed as $d(x,y)$. Vectors $x^i(\theta)$, $0<\theta\leq T$ are not available itself. Therefore the distance between two cycles $x^i(t)$ and $x^j(t)$, $0<t\leq T$ were approached by $$d^2(x^i, x^j) = \sum_{t=0}^{T} d^2(t), d(t) = \min_{\tau \in (-\tau_{max}, \tau_{max})} \|x^i(t) - x^j(t+\tau)\|, \quad (10)$$

using spline interpolation of signals. Here $\tau_{max}$ is a maximum of phase deviation. According to the definition of local coordinates the time for the estimated limit cycle was considered a phase.

5. Synchronize each artefact with the limit cycle by computing $$t^i(\theta) = \underset{(\theta-\tau_{max}, \theta+\tau_{max})}{\mathrm{argmin}} d(\theta) = \underset{t \in (\theta-\tau_{max}, \theta+\tau_{max})}{\mathrm{argmin}} \|x^i(t) - x^0(\theta))\|. \quad (11)$$

6. Subtract the mean cycle from each artefact in phase space according to the synchronization.
7. Collect all segments in order to obtain whole filtered signal.
8. Present the results in time domain.

Parameters of Algorithms were Chosen as Following:

Degree of the Model.

In order to avoid points of self-intersections on limit cycle in phase space, referring to FIGS. 4 and 5, we use a model of forth degree n=4.

Parameter of Smoothness in Gaussian Convolution.

We decided to apply the same parameter a for all derivative approximations in (Eq. 7). This strategy can assure that approximations of ODEs are identical to original equations up to second-order terms. We use transfer functions as a criterion of suitable $\alpha$. For operators $D^k$ transfer functions have the form:

$$\varphi^{(k)} = const \cdot \omega^{2k} e^{-\alpha^2 \omega^2} \quad (12)$$

Location of its maximum is $$\omega_k^* = \frac{\sqrt{k}}{\alpha}.$$

We use a characteristic frequency calculated from mean of the maxima $$f_c = \frac{1}{3 \cdot 2\pi} \sum_{k=1}^{3} \omega_k^*.$$

In order to simplify calculations of convolutions we restrict to integer number of sampling ticks for $\alpha$. Taking into account sampling rate 48 kHz this leads to optimal $\alpha = 6.25 \cdot 10^{-5}$ sec=3 ticks and $f_c = 3.52$ kHz. This value of $f_c$ agrees the best with observed spectral band for spikes and artefacts. In analyzed signals most energy is concentrated in the band from 0.5 to 8 kHz.

Size of Training Data Set

We took N=1000 artefacts of stimulation (7 sec of observation) to the training set.

Maximal Phase Deviation.

To estimate $\tau_{max}$ we assume that phase deviation reaches the maximum across the artefact peak and we use the sampling distribution of times of artefact maximal peak. Difference between two subsequent peak moments equals $$\Delta t_p(k) = T + \gamma^k(\theta_p) - \gamma^{k-1}(\theta_p) \quad (13)$$

were $\theta_p$ is the phase of peak and $\gamma^k(\theta_p)$ is the phase deviation for k-th artefact. Taking into account the short correlation time of perturbation function we considered $\gamma^k(\theta_p)$ as independent random variables with variance $\sigma_p^2 = \sigma^2(\theta_p)$. In this case it holds $\sigma^2(\Delta t_p) = 2\sigma_p^2$. We estimated $\sigma(\Delta t_p)$ directly from a set of peak times. Then maximal phase deviation was fixed as $\tau_{max} = 3\sigma_p$. In case of asymptotically normal distributed $\gamma^k(\theta_p)$ it corresponds to the confidential level 0.997. For example for the signal #S1529 we obtained $\sigma_p = 2.5927 \cdot 10^{-5}$ sec. The maximal phase deviation was fixed as $\tau_{max} = 3\sigma_p = 7.7782 \cdot 10^{-5}$ sec. Then $\tau_{max}$ was adjusted by rounding to the nearest integer number of sampling ticks (4 ticks in case of sampling rate 48 KHz).

Basic Radius R.

Parameter of radius is calculated according to the variance of observed cycles of artefact. Namely the sampling fractiles are used. As we have mentioned above the cycles $x(\theta)$, $0 < \theta \leq T$ could be considered as normally distributed in Euclidian space $\mathfrak{R}^{nT}$. The difference of two independent x and y is also Gaussian. Thus the random values $\sqrt{2}(x-Ex)$ and $z=x-y$ are identically distributed as well as the Euclidian distances $d^2(x, Ex) = \|x - Ex\|^2$ and $d^2(x,y)/2 = \|z\|^2/2$. While expectation of cycles is not known we estimate distribution density function of $d^2(x,y)/2$. To this aide we generated random pairs of cycles from training set and built a histogram. The position of a maximum we took as a basic radius R that corresponds approximately to the fractiles $q_{0.34}$-$q_{0.35}$. Fractiles or quantiles are essentially points taken at regular intervals from the cumulative distribution function of a random variable. Dividing ordered data into q essentially equal-sized data subsets is the motivation for q-quantiles; the fractiles or quantiles are the data values marking the boundaries between consecutive subsets. More formally, the kth "q"-quantile or fractile of the population parameter X can be defined as the value "x" such that:

$$P(X \leq x) \geq p$$

and $$P(X \geq x) \geq 1 - p$$

where $$p = \frac{k}{q}$$

To calculate fractiles we approximate histograms by $\chi_d^2$ distributions. The effective degrees of freedom d were estimated as 7-8 that leads to fractiles mentioned above. So 34.1-35.4% of cycles have to fall in the R-ball of limit cycle. In our experiments we obtained 35-40% of cycles in the ball of radius R by direct count.

Test of the Algorithm:

Several records from the operating room were used to test the algorithm. Original and filtered signals are shown at the FIGS. 3 to 6. FIGS. 7 to 10 display signal sliced into sets of stimulation-period windows before and after filtering. The figures demonstrate the shape of the original artefacts and residuals left after full processing. Also we can see the spikes of neurons.

Artefact Spike Ratio (ASR) before and after signals filtering in phase space and time domain are presented in FIG. 14. Noise Spike Ratio (NSR) for the records is also calculated to compare with ASR after filtering. NSR represents the value that could be achieved by ASR in case of ideal filtration.

Phase portraits in 3D of appropriate artefact sets are depicted in the FIGS. 12 and 13. In the FIGS. 12 and 13, we can see spike trajectories (smaller orbit) of firs record from the FIG. 3.

To compare the quality of signal description by standard model with additive noise according to prior art and phase model (Eq. 2) the appropriate standard deviations of the residuals were calculated. We estimated standard deviations $\sigma_\xi(t)$, $0 < t \leq T$ of additive noise $\xi_k(t)$ in the model (Eq. 1) and $\sigma_{n_1}(\theta)$, $0 < \theta \leq T$, standard deviations of $n_1(t)$, the first coordinates of the vectors of normal deviation (Eq. 5). Values $n_1(t)$ present the residuals of artefacts in time domain for the model (Eq. 2). We can see that phase model produces much smaller variances especially close to the peak. Exact characteristics of $\sigma$-curves are shown in the FIG. 15.

According to the invention, nonlinear oscillation model allows reducing 2-5 times the standard deviation of the residual of artefact of stimulation in comparison with standard model with additive noise and provides much better results of filtering then presented in previous research.

Example

Eight records collected from five human patients during DBS surgery were used to test the algorithm. Neuronal activity is recorded before, during, and after high-frequency stimulation within the subthalamic nucleus, Globus Pallidus or Substantia Nigra (for some records the post-stimulation segment is not available). Stimulation as produced using a Medtronic external stimulator, and the neuronal signals (measured in volts after amplification) were captured using the AlphaOmega Microguide™ recording system. The recordings, using a sampling rate of 48 kHz, had 9 to 100 seconds duration, the stimulation lasting for 7-80 seconds. Periodic stimuli were delivered through microelectrodes placed 2 mm apart in the same brain nucleus, with a frequency of 130 Hz (i.e. with period approx 370 sampling ticks) and a pulse width of 60 μs. The pulse current intensities were in the range of 1000 μA-6000 μA.

In order to explore the algorithm's behaviour depending on artefact amplitude, we constructed a set of artificial signals with predefined ASR. In the recordings (6-second segments) containing artefacts with no neuronal activity, another signal with single-neuron spikes and no stimulation was added. Appropriate constant K gives the desired value of ASR:

$$X_{Syntethic}(t) = X_{Artefacts}(t) + K X_{Single-Neuron}(t).$$

Collection of such signals for ASR from 2 to 20 was generated.

To compare the quality of signal description by the standard model with additive noise according to the equation $x_{St}(t+kT) = x_{St}^0(t) + \xi_k(t)$, $0 < t \leq T$, and model according to the equation $$\frac{d^n x_{St}}{dt^n} = f\left(x, \ldots, \frac{d^{n-1} x_{St}}{dt^{n-1}}\right) + F\left(x_{St}, \ldots, \frac{d^{n-1} x_{St}}{dt^{n-1}}, t\right),$$

the appropriate phase dependent standard deviations of the residuals STD(t), $0 < t \leq T$ were calculated, as represented in FIG. 16 wherein dash line is a representation of signal by the model with additive noise according to the equation $x_{St}(t+kT) = x_{St}^0(t) + \xi_k(t)$, $0 < t \leq T$ and continuous line is a representation phase-dependent artefact STDs based on the representation of signal by the nonlinear model of oscillations according to the equation $$\frac{d^n x_{St}}{dt^n} = f\left(x, \ldots, \frac{d^{n-1} x_{St}}{dt^{n-1}}\right) + F\left(x_{St}, \ldots, \frac{d^{n-1} x_{St}}{dt^{n-1}}, t\right).$$

We estimated standard deviation $\sigma_\xi(t)$, $0 < t \leq T$ of additive noise $\xi_k(t)$ in the model according to the equation $x_{St}(t+kT) = x_{St}^0(t) + \xi_k(t)$, $0 < t \leq T$ and $\sigma_{n_1}(\theta)$, $0 < \theta \leq T$, standard deviations of $n_1(t)$, the first coordinates of the vectors of normal deviation according to the equation $x^i(t(\theta)) = x^0(\theta) + n^i(\theta)$, $0 < \theta \leq T$ Values $n_1(t)$ represent the residuals of artefacts in the time domain for the model according to the equation $$\frac{d^n x_{St}}{dt^n} = f\left(x, \ldots, \frac{d^{n-1} x_{St}}{dt^{n-1}}\right) + F\left(x_{St}, \ldots, \frac{d^{n-1} x_{St}}{dt^{n-1}}, t\right).$$

Eight real data recordings, as described above, were used to estimate STD(t). The phase model according to the equation $$\frac{d^n x_{St}}{dt^n} = f\left(x, \ldots, \frac{d^{n-1} x_{St}}{dt^{n-1}}\right) + F\left(x_{St}, \ldots, \frac{d^{n-1} x_{St}}{dt^{n-1}}, t\right)$$

produces much smaller variances, especially close to the peak (see FIG. 17). The sums of STD across residuals were in average 2.13 times less and the maxima of STD were 1.5-2.1 (1.8 in average) times less for the phase model.

The test intends to reveal what happens to spike trains and spikes themselves in the presence of stimuli and cleaning procedures. Spike trains obtained from an original signal of neuronal activity $X_{single-Neuron}(t)$ before mixing with artefacts and after full processing were compared. A simple threshold filter was used for spike trains extraction. The percentages of spikes found at their correct positions in the processed signal were measured. Let us note that the summation of signals with coefficient K changes the spike-noise ratio. The graphs of errors of spike detection depending on ASR and corresponding SNR are depicted in the FIGS. 18 and 20. FIG. 19 represents variances of two first principal components of spikes depending on ASR. We can see that spikes rest practically intact up to ASR about 10-12. Moreover, note that ASR=0 corresponds to the original neuronal activity with no stimulation added.

The recordings described above were used to test the algorithm on real data. The signals are characterized by ASR $\in$ [1.3, 14], ANR $\in$ [3, 160] and SNR $\in$ [1.4, 5.1]. Examples of original and filtered signals are shown in FIGS. 3 to 6. FIGS. 7 to 10 displays the signal sliced into sets of stimulation-period windows, before and after filtering. The figure demonstrates the shape of the original artefacts and of the residuals left after full processing. One can see also the neuronal spikes. The phase portraits in 3D of appropriate artefact set are depicted in the FIGS. 12 and 13.

Dependences between Artefact Spike Ratio (ASR) before and after signals filtering, both in phase space and time domain are presented in the FIG. 21. For comparison, we have also shown such results for synthetic data. Results for eight real records and synthetic signals are in a good fit. The use of phase space filtering produced smaller artefact residuals in all experiments with real and synthetic data: $ASR_{Time}/ASR_{PhaseSpace} > 1$. Here $ASR_{PhaseSpace}$ and $ASR_{Time}$ are the ASR after processing in phase space and in time domain. $ASR_{Phase\ Space} = 0.239$ and $ASR_{Time} = 0.537$ in average for the real data set (initial ASR $\in$ [1.3, 14]) and $ASR_{Phase\ Space} = 0.418$ and $ASR_{Time} = 1.151$ in average for the synthetic data (initial ASR $\in$ [2, 20]). An advantage of phase space filtering augments with increasing of initial ASR of the signal. The ratio of artefact residuals exceeds two, $ASR_{Time}/ASR_{PhaseSpace} > 2$, in the experiments with both real and synthetic data if ASR before filtering surpasses four. Namely $ASR_{PhaseSpace}/ASR_{Time} = 2.87$ on average for real data set and $ASR_{PhaseSpace}/ASR_{Time} = 2.81$ on average for the synthetic data set if ASR>4.

Accordingly, methods and systems for processing neural signals in a brain-computer interface have been described above. The individual system components described herein may be specifically constructed for performing various processes and operations of the invention or they may include a general purpose computer or computing platform selectively activated or reconfigured by program code to provide the necessary functionality. The processes disclosed herein are not inherently related to any particular computer or apparatus, and may be implemented by any suitable combination of hardware, software, and/or firmware. For example, various general purpose machines may be used with programs written in accordance with the teachings of the invention, or it may be more convenient to construct a specialized apparatus or system to perform the required methods and techniques.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. Method for filtering a signal of neuronal activity during a high frequency deep brain stimulation (DBS) to remove a stimulus artefact in an observed signal, comprising:
   using an analysis unit:
   i) approximating the observed signal trajectories in phase space, by considering the observed signal as a sum of the stimulation artefacts induced by the signal of stimulation, and by assuming that the signal of stimulation is a solution of an ordinary differential equation including a self-oscillating system with stable limit cycle, ii) slicing the observed signal and its derivative into segments, each segment corresponding to a period of stimulation, and selecting N periods among the segments, iii) collecting the N selected periods of stimulation into a training set, iv) estimating the limit cycle of the self-oscillating system using the training set, v) synchronizing each stimulation artefact of the observed signal with the estimated limit cycle, vi) subtracting the estimated limit cycle from each artefact in phase space according to the synchronization, vii) collecting all segments in order to obtain a whole filtered signal, and viii) presenting the results in the time domain.

2. Method according to claim 1 wherein the signal trajectories in phase space are approximated by computing a smoothed signal and approximation of signal derivatives using Gaussian convolution.

3. Method according to claim 2 wherein the Gaussian convolution is calculated for a characteristic frequency between 3 and 4 kHz for a sampling rate of 48 kHz.

4. Method according to claim 3 wherein the characteristic frequency is equal to 3.52 kHz.

5. Method according to claim 1 wherein the center of each segment is near the highest of signal peaks in the observed signal.

6. Method according to claim 1 wherein the segments are selected randomly.

7. Method according to claim 1 wherein the limit cycle of the self-oscillating system is estimated by using the element from the training set that provides the maximum of probability density in the neighborhood of the limit cycle.

8. Method according to claim 1 wherein the self-oscillating system with stable limit cycle is a self-oscillating system of forth degree.

9. Method according to claim 1 wherein the training set, collected from N selected periods, comprises at least 1000 artefacts of simulation.

10. A non-transitory computer medium comprising instructions that, when executed, cause a processor to perform the steps of:

i) approximating observed signal trajectories in phase space, by considering the observed signal as a sum of stimulation artefacts induced by a signal of stimulation, and by assuming that the signal of stimulation is a solution of an ordinary differential equation including a self-oscillating system with stable limit cycle, ii) slicing the observed signal and its derivative into segments, each segment corresponding to a period of stimulation, and selecting N periods among the segments, iii) collecting the N selected periods of stimulation into a training set, iv) estimating the limit cycle of the self-oscillating system using the training set, v) synchronizing each stimulation artefact of the observed signal with the estimated limit cycle, vi) subtracting the estimated limit cycle from each artefact in phase space according to the synchronization, vii) collecting all segments in order to obtain a whole filtered signal, and viii) presenting the results in the time domain.

11. Non-transitory computer medium according to claim 10 wherein the signal trajectories in phase space are approximated by computing a smoothed signal and approximation of signal derivatives using Gaussian convolution.

12. Non-transitory computer medium according to claim 11 wherein the Gaussian convolution is calculated for a characteristic frequency between 3 and 4 kHz for a sampling rate of 48 kHz.

13. Non-transitory computer medium according to claim 12 wherein the characteristic frequency is equal to 3.52 kHz.

14. Non-transitory computer medium according to claim 10 wherein the center of each segment is near the highest of signal peaks in the observed signal.

15. Non-transitory computer medium according to claim 10 wherein the segments are selected randomly.

16. Non-transitory computer medium according to claim 10 wherein the limit cycle of the self-oscillating system is estimated by using the element from the training set that provides the maximum of probability density in the neighborhood of the limit cycle.

17. Non-transitory computer medium according to claim 10 wherein the self-oscillating system with stable limit cycle is a self-oscillating system of forth degree.

18. Non-transitory computer medium according to claim 10 wherein the training set, collected from N selected periods, comprises at least 1000 artefacts of simulation.

* * * * *

UNITED STATES PATENT AND TRADEMARK OFFICE
CERTIFICATE OF CORRECTION

PATENT NO. : 8,620,420 B2  
APPLICATION NO. : 12/597196  
DATED : December 31, 2013  
INVENTOR(S) : Tetiana Aksenova et al.

Page 1 of 1

It is certified that error appears in the above-identified patent and that said Letters Patent is hereby corrected as shown below:

On the Title Page, please correct the following item:

Item [73] Change the name of the Assignee from Institute National de la Sante et de la Rescherche Medicale (INSERM) to --Institut National de la Sante et de la Rescherche Medicale (INSERM)--

Signed and Sealed this  
Twenty-fourth Day of June, 2014

Michelle K. Lee  
*Deputy Director of the United States Patent and Trademark Office*

UNITED STATES PATENT AND TRADEMARK OFFICE
CERTIFICATE OF CORRECTION

PATENT NO.         : 8,620,420 B2
APPLICATION NO.    : 12/597196
DATED              : December 31, 2013
INVENTOR(S)        : Tetiana Aksenova et al.

Page 1 of 1

It is certified that error appears in the above-identified patent and that said Letters Patent is hereby corrected as shown below:

On the Title Page, please correct the following item:

Item [73] Institute National de la Sante et de la Rescherche Medicale (INSERM) to --Institut National de la Sante et de la Recherche Medicale (INSERM)--

Signed and Sealed this
Twenty-sixth Day of May, 2015

Michelle K. Lee
*Director of the United States Patent and Trademark Office*